United States Patent
Vollrath et al.

(10) Patent No.: US 6,277,062 B1
(45) Date of Patent: Aug. 21, 2001

(54) NON-INVASIVE PENILE ERECTION DEVICE

(75) Inventors: Andrew J. Vollrath, 3524 Superior Ave., Sheboygan, WI (US) 53083; Ji Ji Secong Vollrath, Sheboygan, WI (US); Gwo Bao Wu, Taipei (TW)

(73) Assignee: Andrew J. Vollrath, Sheboygan, WI (US)

(*) Notice: Subject to any disclaimer, the term of this patent is extended or adjusted under 35 U.S.C. 154(b) by 0 days.

(21) Appl. No.: 09/575,323

(22) Filed: May 19, 2000

Related U.S. Application Data

(62) Division of application No. 09/328,059, filed on Jun. 8, 1999, now Pat. No. 6,117,069, which is a division of application No. 08/895,130, filed on Jul. 16, 1997, now Pat. No. 5,951,460.

(51) Int. Cl.$^7$ .................................................. A61F 5/00
(52) U.S. Cl. ............................................ 600/38; 600/41
(58) Field of Search ................. 600/38–41; 128/897–898

(56) References Cited

U.S. PATENT DOCUMENTS

| | | |
|---|---|---|
| 4,224,933 | 9/1980 | Reiling . |
| 4,641,638 | 2/1987 | Perry . |
| 4,723,538 | 2/1988 | Stewart . |
| 4,753,227 | 6/1988 | Yanuck, Jr. . |
| 4,856,498 | 8/1989 | Osbon . |
| 5,020,522 * | 6/1991 | Stewart ................................ 600/38 |
| 5,125,890 | 6/1992 | Merrill . |
| 5,195,943 | 3/1993 | Chaney . |
| 5,234,402 | 8/1993 | Osbon . |
| 5,306,227 | 4/1994 | Osbon . |
| 5,327,910 | 7/1994 | Fiynn . |
| 5,344,389 | 9/1994 | Walsdorf . |
| 5,628,329 | 5/1997 | Bennett . |

FOREIGN PATENT DOCUMENTS

| | | |
|---|---|---|
| 347300 | 8/1960 | (CH) . |
| 83211373 | 10/1995 | (TW) . |

* cited by examiner

Primary Examiner—Eric F. Winakur
Assistant Examiner—Michael C Astorino
(74) Attorney, Agent, or Firm—Sokol Law Office

(57) ABSTRACT

The present invention relates to a non-invasive penile erection device having a constrictor ring designed to fit against the base of a male genital or penis, and a diaphragm seal that forms a substantially air tight seal against the constrictor ring. The constrictor ring is designed to comfortably and securely fit the base of the penis. The substantially air tight seal enables the pump to produce vacuum pressures of over 17 inches of mercury. The diaphragm seal is designed to collapse around the constrictor ring and remain on during sexual activity. The diaphragm seal cooperates with the constrictor ring to apply pressure to the surface of the penis. The placement of the constrictor ring on the base of the penis and the greater vacuum pressure achieved by the device tend to draw the root or "oz" of the penis into the constrictor ring so that a more natural erection is achieved and maintained after the vacuum tube is removed. Removal of the diaphragm seal reduces the total pressure being exerted on the male genital, which causes the genital to deflate and facilitates the removal of the constrictor ring. The vacuum tube has an open end with a blunt area to reduce the pinching of the individual's skin between the tube and their hop bone. The open end of the vacuum tube also includes a double flange to facilitate accurate placement of the diaphragm on the tube. The erection device can be provided as a kit containing a rigid vacuum tube, and electric pump, and several diaphragm seals and constrictor rings of various sizes to achieve a custom fit and optimum results.

7 Claims, 9 Drawing Sheets

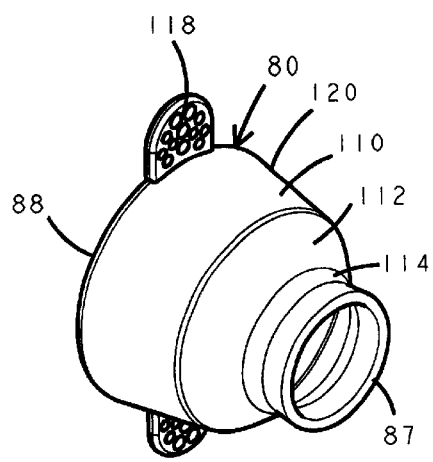 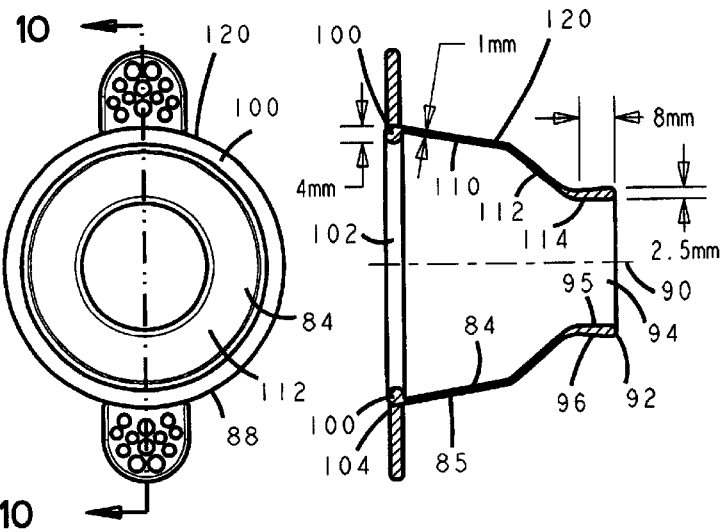
FIG. 8  FIG. 9  FIG. 10
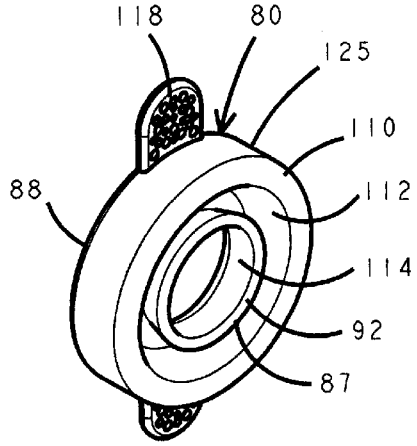 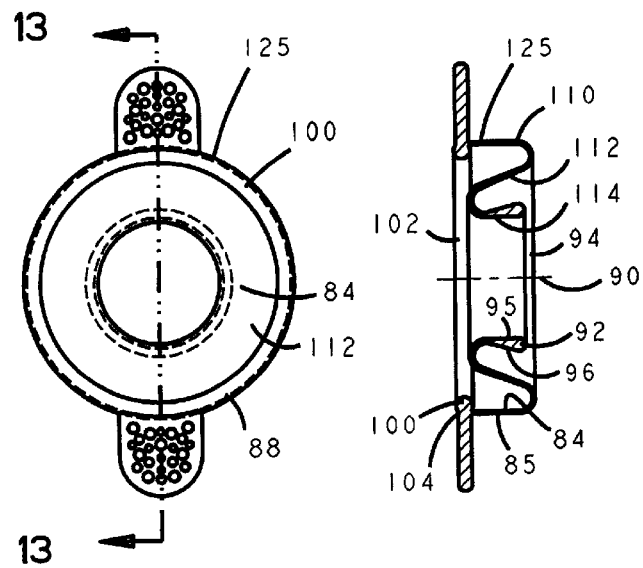
FIG. 11  FIG. 12  FIG. 13

NON-INVASIVE PENILE ERECTION DEVICE

This application is a divisional of Ser. No. 09/328,059 filed Jun. 8, 1999 U.S. Pat. No. 6,117,069 which is a Div. of Ser. No. 08/895,130 filed Jul. 16, 1997 U.S. Pat No. 5,951, 460.

TECHNICAL FIELD

The present invention relates to a non-invasive penile erection device using a vacuum tube and a diaphragm that seals against a constrictor ring placed at the base of the male genital to provide a comfortable customized fit at greater vacuum pressures to produce a more natural erection.

BACKGROUND PRIOR ART

A variety of non-invasive, vacuum type penile inflation devices are available. These inflation devices use external vacuum pressure to replace the body's natural ability to inflate the male genital or penis with blood. The devices typically utilize cylindrically shaped vacuum tube for receiving the penis, a diaphragm for sealing the open end of the vacuum tube around the penis and a pump for evacuating or removing air from the vacuum tube. When air is removed from inside the tube, the decrease in pressure causes blood to enter and inflate the male genital. a constrictor ring is typically placed around the male genital after it is inflated to maintain the inflated state of the penis when the vacuum tube is removed. Examples of such devices are shown in U.S. Pat. Nos. 4,64441,638 to Perry, 4,753,227 to Yanuck, Jr., 4,856, 498 to Osbon, 5,125,890 to Merrill, and 5,344,389 to Walsdorf, the contents of which are incorporated by reference.

One shortcoming of conventional penile inflation devices is that the diaphragm does not form a sufficiently air tight seal to produce a desired amount of vacuum pressure inside the tube. Even when gel lubricants are applied to the diaphragm and male genital to improve the seal, air tends to leak between the diaphragm and the male genital. This air leakage reduces the amount of vacuum pressure attained inside the tube and the amount of inflation and stiffness of the male genital. Conventional penile inflation devices achieve about 14 to 16 inches of mercury of vacuum pressure, while a fully inflated, usable erection often requires about 17 to 22 inches of mercury of vacuum pressure.

An additional shortcoming with the prior art is that the inflation devices do not inflate and maintain the penis in an erect and usable position. Conventional constrictor rings are designed to fit on and secure to the substantially flat shaft portion of the penis. The rings are not intended to fit around the increasingly larger diametered base of the penis located adjacent the groin of the individual, especially when inflated. The increasingly wider base creates a slope that causes the constrictor ring to slide off the base and onto the shaft of the penis. Conventional constrictor ribs are also not designed to allow the root or "oz" of the penis, which extends inwardly of the groin of the individual, to be drawn into the constrictor ring. When the vacuum tube is removed, only that portion of the shaft of the penis downstream of the constrictor ring remains inflated. The base and root of the penis remain or return to flaccid state and the penis does not achieve and maintain a natural erect position.

A still further problem with the prior art is that the flaccid base and root portions of the penis upstream of the constrictor ring create a "joint" about which the inflated shaft portion of the penis may bend. The inflated portion of the penis must be manipulated by hand during use, which can be especially difficult for paraplegic and quadriplegic individuals or their partner.

A further problem of the prior art is that conventional constrictor rings used in various inflation devices are painful due to their narrow width and generally "rubber band" like shape. The edges of the constrictor ring dig into the skin of the individual and cause substantial pain.

A still further problem with conventional designs is that it is difficult to position the constrictor ring on the base or root of the male genital after it is place on the penis. The user must grip the edges of the narrow rubber band shaped constrictor ring to adjust the constrictor ring and attempt to work it onto the base after its initial placement on the shaft of the penis. This can be quite difficult when the edges of the constrictor ring are digging into the skin.

A still further problem of conventional designs is that the lubricants used to help form the seal between the diaphragm and the male genital are messy. Lubricant invariably spreads all over the inflation device, the hands and body of the individual, and the surroundings.

A still further problem of the prior art is that the diaphragm and constrictor ring so not fit all individuals with equal comfort and equal results. Different individuals require differently sized constrictor rings and diaphragms. A trial and error approach to obtaining a correctly sized constrictor ring and diaphragm can be inconvenient and embarrassing given the nature of the product involved.

A still further problem with the prior art assemblies is that the manufacturing costs can be excessive. The cost and umber of components making up the penile erection device should be kept to a minimum. The erection device should also cooperate with existing vacuum tube and pump designs when possible to avoid expensive and time consuming manufacturing modifications.

A still further problem with the prior art assemblies is that the open end or rim of the tube digs into the groin area of an individual when vacuum pressure is applied inside the tube. The individual's skin is pinched between the rim of the tube and their hip bone. This is especially painful when vacuum pressures near 15 inches of mercury and up are achieved.

A still further problem with the prior art assemblies is that the diaphragm seal is not always secured to the tube in the same location. Individuals do not always seat the outer end of the diaphragm in its proper location against the lip of the tube. The outer end of the diaphragm may be pulled too far back over the lip of the tube, or one side of the seal may be pulled over the lip too far. These inconsistencies in placement result in inconsistencies in the stretching of the diaphragm seal, which in turn results in inconsistencies in the operation of the diaphragm seal, such as the shape of the diaphragm seal when flexed during use and the size and shape of the inner end of the diaphragm seal.

A still further problem with the prior art assemblies is that they are cumbersome to operate. The individual must hold the tube firmly against his groin with one hand while repeatedly squeezing the hand pump with the other. The need for lubricants only adds to the mess and difficulty in using these devices.

A still further problem with the prior art assemblies is that the inner edge of a conventional diaphragm seal has a round or circular cross sectional shape. This round shape only permits a small surface area of the inner end to engage the penis. Any pressure applied by the diaphragm seal to the penis to aid in the enlargement of the penis is applied over this relatively small surface area. It is believed that the application of pressure in this manner may restrict arterial blood flow to the penis, thereby reducing the effectiveness of the device.

A still further problem with the prior art assemblies is that the diaphragm seal is designed to be removed after the penis has been enlarged. The bulky, outwardly projecting, cone-like shape of the diaphragm would be noticeable impediment to the individual and his partner if it were left in place during sexual activity.

A still further problem with the prior art assemblies is that the rubber band can be difficult and painful to remove after use. Like a ring stuck on a swollen finger, the rubber band pinches into the sides of the penis. There are frequently no handles for griping conventional rubber band designs for removal. Typical methods for removing the rubber bands and constrictor rings are painful because the penis remains enlarged when the rubber band or constrictor ring is removed.

A still further problem with the prior art assemblies is that the material used to make conventional vacuum tubes can be cracked or otherwise damaged during storage and handling. The risk of harming an individual could arise if a damaged tube is subjected to high vacuum pressures during use.

The present invention is provided to solve these and other problems.

SUMMARY OF THE INVENTION

The present invention relates to a non-invasive penile erection device having a constrictor ring designed to fit against the base of a male genital or penis, and a diaphragm seal that forms a substantially air tight seal against the constrictor ring. The constrictor ring is designed to comfortably and securely fit the base of the penis. The substantially air tight seal enables the pump to produce vacuum pressures of over 17 inches of mercury. The diaphragm seal is designed to collapse around the constrictor ring and remain on during sexual activity. The diaphragm seal cooperates with the constrictor ring to apply pressure to the surface of the penis. The placement of the constrictor ring on the base of the penis and the greater vacuum pressure achieved by the device tend to draw the root or "oz" of the penis into the constrictor ring so that a more natural erection is achieved and maintained after the vacuum tube is removed. Removal of the diaphragm seal reduces the total pressure being exerted on the male genital, which causes the genital to deflate and facilitates the removal of the constrictor ring. The vacuum tube has an open end with a blunt area to reduce the pinching of the individual's skin between the tube and their hip bone. The open end of the vacuum tube also includes a double flange to facilitate accurate placement of the diaphragm on the tube. The erection device can be provided as a kit containing a rigid vacuum tube, an electric pump, and several diaphragm seals and constrictor rings of various sizes to achieve a custom fit and optimum results.

One advantage of the present invention is its ability to inflate the shaft, base and root protions of the male genital. The constrictor ring is designed to securely fit the base of the penis and draw a portion of the root of the penis into the constrictor ring when vacuum pressure is applied to the inside of the vacuum tube. The inflation of the base and root portions of the penis causes the penis to rise to a more natural erect position. The constrictor ring also maintains the penis in an erect position after the vacuum tube is removed.

An additional advantage of the present invention is that the hands of the individual may remain free during use bacuse the base of the penis does not become flaccid after the vacuum tube is removed to from a "joint" about which the shaft of the penis can bend.

A further advantage of the present invention is that the constrictor ring is designed to be easily positioned onto the base of the male genital with the tabs of the ring abutting the groin of the individual. The tabs of the constrictor ring enable the individual to work the ring securely onto the increasing diameter or sloped shape of the base of the male genital. The constrictor ring is shaped to have an increasing inside diameter down the length of the ring moving from the outer edge of the tubular portion to the inner end of the conical portion. This increasing inside diameter enables the ring to stay fixed on the base of the penis both during inflation and use without sliding down the shaft of the penis.

A still further advantage of the present invention is that the inner and outer ends of the constrictor ring are rounded to provide a comfortable fit by helping to prevent the constrictor ring from digging into the skin of the individual.

A still further advantage of the present invention is that the diaphragm is disigned to form a substantially air tight seal against the constrictor ring. The tubular portion of the constrictor ring has a predetermined diameter that increases slightly moving from the outer end toward the inner end of the constrictor ring. The inner end of the diaphragm has a thick, rounded shank with a predetermined diameter that is substantially equivalent to the diameter of the outer end of the tubular portion of the constrictor ring. When air is removed from the vacuum tube, the tubular portion of the constrictor ring slides into the diaphragm seal to form a relatively air tight seal. This seal enables the vacuum pump to obtain a sufficient level of vacuum pressure to inflate the penis and draw a portion of the root of the penis into the constrictor ring. This allows the penis to achieve a more natural erection both while the vacuum tube is in use and after the vacuum tube has been removed.

A still further advantage of the present invention is that no messy lubricants are necessary to form the seal between the constrictor ring and the diaphragm.

A still further advantage of the present invention is its reliability and ease of use. A loader is provided for placing the ring on the base of the penis. The tabs enable the individual to slide the ring from the narrow receiving end, down the length of the loader to its wider open end. After the penis is inserted into the open end of the loader, the individual can grip the tabs to pull the ring off the loader and onto the base of the penis. The tabs also permit the individual to further advance the ring down the base of the penis so that a portion of the root of the penis can be inflated during use. The ease with which an individual can position the constrictor ring on the base of the penis helps ensure that a more natural erection is attained by the individual during each use.

A still further advantage of the present invention is that a plurality of differently sized diaphragm seals and constrictor rings can be provided in a kit that includes all the penile erection device components. The individual can select the diaphragm and constrictor ring that fits them best for a customized, comfortable fit that produces good results in the privacy of their own home. Inconvenient and embarrassing trips to a doctor or store are not necessary.

A still further advantage of the present invention is found in its inexpensive component costs and its relative ease of manufacture. For example, the present vacuum tube can be manufactured using relatively inexpensive conventional plastic tubes. The flexible diaphragm and constrictor ring designs can be efficiently incorporated into a conventional; vacuum tube and pump designs so that expensive and time consuming manufacturing costs are avoided.

A still further advantage of the present invention is that the open end of the tube has a blunt area spread out the force and reduce the among of pressure applied by the tube to the groin area of the individual when vacuum pressure is achieved inside the tube. This reduces the amount of pain and pinching of the individual's skin between the outer end of the tube and their hip bone. This is especially important when vacuum pressures around or above 16 inches of mercury are achieved.

A still further advantage of the present invention is that the outer end of the vacuum tube is provided with a double flange for receiving the outer end of the diaphragm seal. The double flange shape provides a positioning channel for receiving the outer end of the diaphragm seal. Individuals can more easily secure the diaphragm seal to the tube in its proper centered location each time it is placed on the tube. The outer end of the diaphragm seal is not pulled too far back over the lip of the tube. The outer end of the diaphragm seal is not pulled too far back over the lip of the tube, nor is one side of the diaphragm seal pulled over the lip too far. This consistent placement results in a consistent, even stretching of the diaphragm seal over the tube. This results in the consistent operation of the diaphragm seal. The inner end is stretched more evenly to achieve a circular shape for engaging the penis, so that the diaphragm applies pressure evenly around the surface of the male genital.

A still further advantage of the present invention is that it is easy to operate. The control plug and electric pump facilitate easy operation of the device. The vacuum gauge, power switch and vacuum relief valve are centrally located for ease of use.

A still further advantage of the present invention is that the inner edge of a conventional diaphragm seal has a "tear drop" cross sectional shape. This tear drop shape enables a larger surface area of the inner end to engage the surface of the genital. Pressure applied by the diaphragm seal to the genital to aid in the inflation of the genital is applied over this larger surface area. It is believed that the application of pressure in this manner facilitates arterial blood flow to the penis, thereby increasing the effectiveness of the device.

A still further advantage of the present invention is that the diaphragm seal is designed to collapse over the constrictor ring. When about 17 inches of mercury in vacuum pressure is achieved, the diaphragm seal inverts into an "S" shape. After the male genital has been full enlarged and the vacuum tube is removed, the diaphragm collapses into a relatively compact "S" shape around the constrictor ring. When in this collapsed shape, the diaphragm is not a noticeable impediment to the individual and his partner during sexual activity.

A still further advantage of the present invention is that the cooperating diaphragm seal and constrictor ring can be more easily and painlessly remove after use. The diaphragm seal is removed first. This is easily accomplished by gripping the handles and pulling the diaphragm back into its initial outwardly projecting cone shape. This outwardly projecting cone shape is more easily pulled off the enlarged male genital. The removal of the diaphragm seal eliminates some of the pressure exerted on the genital. This allows some of the blood to flow out of the genital and reduces its enlarged state. The constrictor ring can then be more easily removed from the partially deflated penis.

Other features and advantages of the invention will be apparent from the following specification taken in combination with the following drawings.

BRIEF DESCRIPTION OF DRAWINGS

FIG. 8 is a perspective view of the diaphragm seal in a relaxed position.

FIG. 9 is a top view of the diaphragm seal in the relaxed position.

FIG. 10 is a cross-sectional view taken along line 10—10 of FIG. 9.

FIG. 11 is a perspective view of the diaphragm seal in a collapsed position.

FIG. 12 is a top view of the diaphragm seal in the collapsed position.

FIG. 13 is a cross-sectional view taken along line 13—13 of FIG. 12

DETAILED DESCRIPTION

Figure 1:
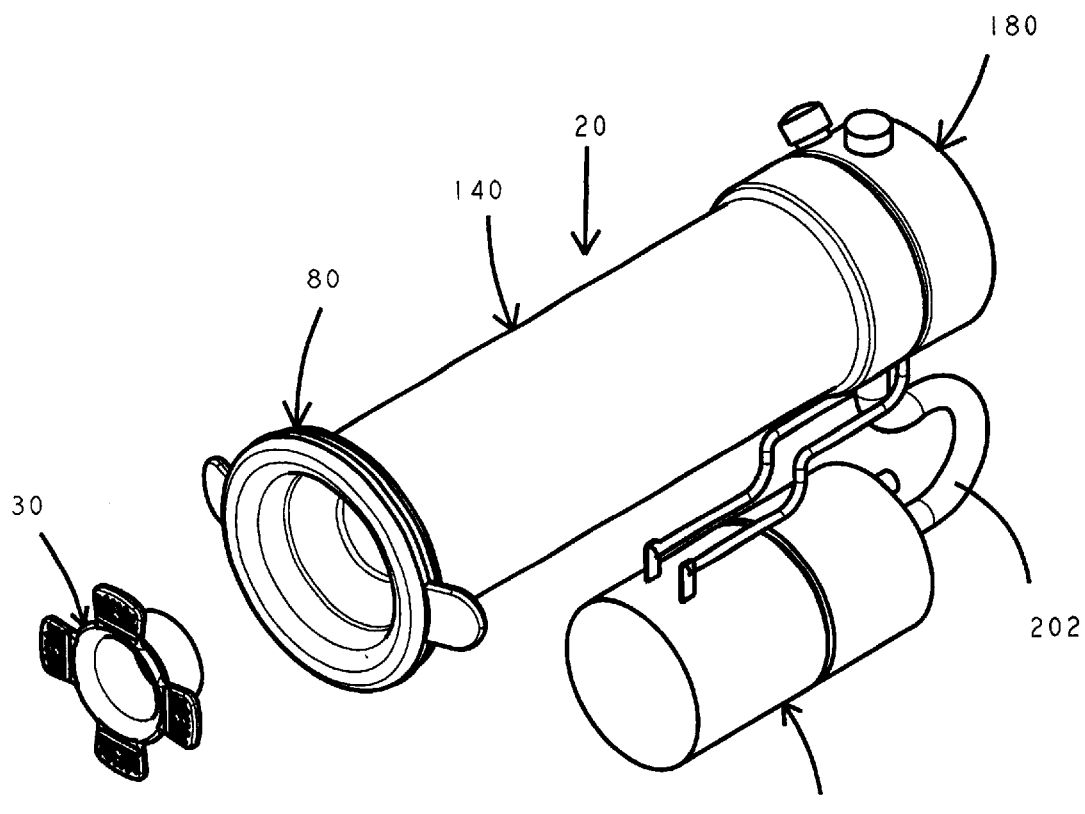
FIG. 1 is a perspective view of a penile erection device of the present invention including a constrictor ring, a vacuum tube having a diaphragm seal at one end and a control plug on the other, and electric power pump connected to the control plug.

While this invention is susceptible of embodiments in may different forms, there is shown in the drawings and will herein be described in detail, a preferred embodiment of the invention with the understanding that the present disclosure is to be considered as an exemplification of the principles of the invention and is not intended to limit the broad aspects of the invention to the embodiment illustrated.

Figure 24:
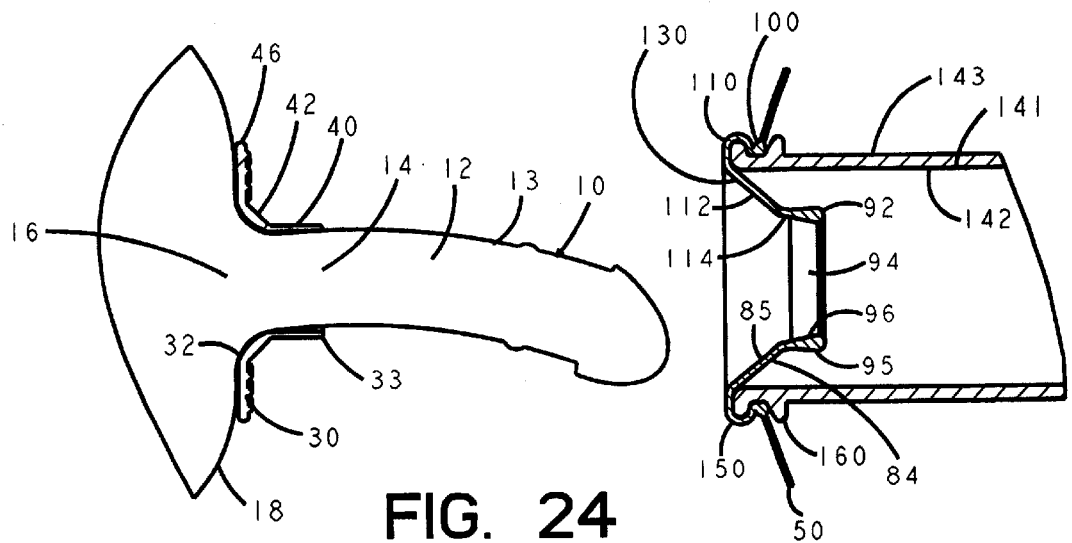
FIG. 24 is a cross-sectional view showing the constrictor ring secured to the base of a flaccid male genital with the vacuum tube and diaphragm seal aligned to receive the male genital.

As shown in FIGS. 1 and 24, the present invention relates to a vacuum type penile erection device for a male genital 10 having a shaft 12 with a surface 13, a base portion 14 and a root portion 16 located beneath the surface of the groin 18 of an individual. The erection device 20 includes a constrictor ring 20 placed around the base of the male genital 10, a flexible diaphragm 80 that seals around the constrictor ring and is secured to an open end of a vacuum tube 140. The male genital 10 is then inserted through the diaphragm seal 80 and into the vacuum tube 140. A control plug 180 sealing an opposite end of the vacuum tube 140 is used in conjunction with an electric pump 200 to evacuate or removing air from the tube. The constrictor ring 30 and diaphragm seal 80 combine to achieve an amount of pressure around the surface 13 of male genital 10 necessary to maintain the genital in an erect position after the vacuum tube 140 is removed.

As best shown in FIGS. 3–7, the constrictor ring 30 is formed from an integral piece or main body 31 of soft, durable and flexible rubber to facilitate comfort and bending and stretching during use. Although the constrictor ring 30 is preferably made of synthetic natural rubber, it should be under stood that the materials having similar characteristics may be used. The constrictor ring 30 has inner and outer ends 32 and 32 and inside and outside surface 34 and 35. A tubular portion 40 is located proximal the outer end 33. A conical portion 42 is located proximal the inner end 32. Four tabs or handles 45–48project outwardly from the inner end 32 of the conical portion 42. The tubular portion 40 has a length of about 0.50 of and inch and thickness of about 0.045 of an inch. The conical portion 42 has a length of about 0.25 of an inch and a varying thickness due to its rounded inside surface 34 of the inner end 32. The conical portion 42 is generally thicker than that or the tubular portion 40. The tubular portion 40 forms an opening having a predetermined diameter of about one inch at the outer end 33, but rings of various diameters are provided to obtain a custom fit, as discussed below.

The inner and outer ends 32 and 33 of the constrictor ring 30 are rounded for comfort and ease of use. The inside surface 34 of the inner end 32 is rounded to a radius of about 0.025 of an inch to provide a comfortable fit and accommodate the typically increasing diameter of the base 14 of the male genital 10. Although the inside surface of 34 of the inner end 32 is rounded, it should be understood that the inside surface may have a different arcuate shape. The outside surface 35 of the conical portion 42 is chamfered at about a 45 degree angle. The outer end 33 of the constrictor ring 20 is rounded on both its inside and outside surfaces 34 and 35 to a radius of about 0.01 of an inch. The inside surface 34 of the outer end 33 is rounded to provide a comfortable fit. The outside surface 35 of the outer end 33 is rounded to facilitate sliding engagement of the inner shank 92 of the diaphragm seal 80 during use, as discussed below.

The inside diameter of the inside surface 34 of the tubular portion 40 increases slightly and continuously heading away from outer end 33 and toward inner end 32. The increase in inside diameter is more pronounced in the conical portion 42 due to the rounding of the inside surface 34 of the inner end 32 as discussed above. The continuously increasing diameter of the inside surface 34 enables the individual to fit the constrictor ring onto the base 14 of the penis 10 and helps maintain the ring at this location during use. The continuously increasing diameter of the inside surface 34 also helps form the substantially air tight seal between the diaphragm 80 and the constrictor ring 30. Although the constrictor ring 30 is shown as having the diaphragm 80 and the constrictor ring 30. Although the constrictor ring 30 is shown as having a conical portion 42 with a chamfered outside surface 35 that meets the tubular portion 40 at about a 45 degree angle, it should be understood that the outside surface 35 of the conical and tubular portions could form a continuous arcuate or rounded shape.

Each handle 45–48 projects from the conical portion 42 at a 90° angle from its adjacent handle. Each handle also has a common predetermined with dimension. The handles 45–48 inhibit the conical portion 42 of the constrictor ring 30 from stretching during use. The areas between each of the tabs 45–48 form expansion joints in the conical portion 42 which tend to stretch more easily when vacuum is applied to the vacuum tube 220 and the base 14 of male genital 10 inflates. The handles 45–48 have roughened areas 50 on their inside and outside surfaces 34 and 35 to provide a more gripable surface.

As best shown in FIG. 24, the constrictor ring 30 is intended to be placed on the base 14 of the male genital 10 so that the handles 45–48 touch, but do not press into the surface of the groin 18 of an individual. The optimal results are believed to occur when the constrictor ring 30 is placed on the base 14 of a flaccid male genital 10 with the handles in this position. It is in this position that the root 16 of the penis 10 is believed to be most effectively drawn into the constrictor ring 30, as discussed below. A groove 55 is formed into the inside and outside surfaces 33 and 34 of each handle 45–48 near the neck of the handle these grooves 55 facilitate the bending of the handle during use.

Figure 2:
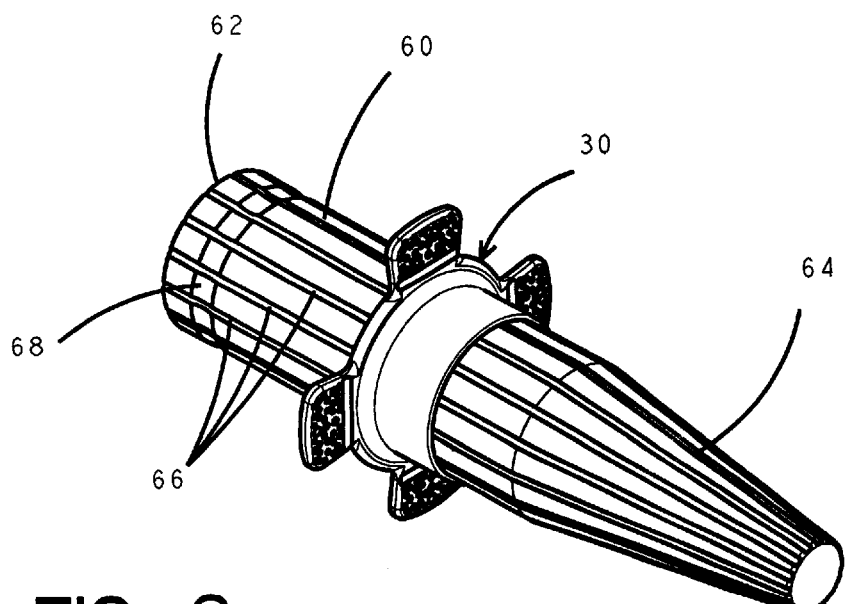
FIG. 2 is a perspective view of a constrictor ring of the present invention placed on a loading tube for installing the constrictor ring on the base of the male genital.
Figure 3:
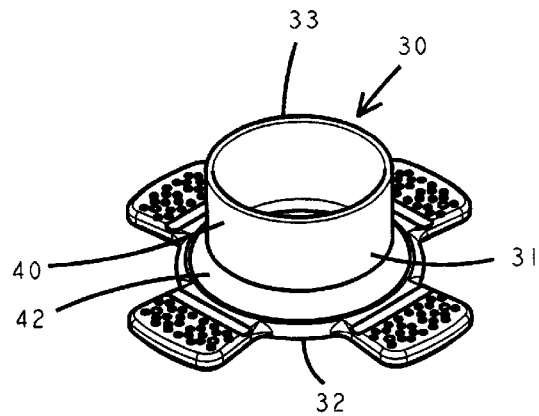
FIG. 3 is a perspective view of the constrictor ring with a four tab design.
Figure 4:
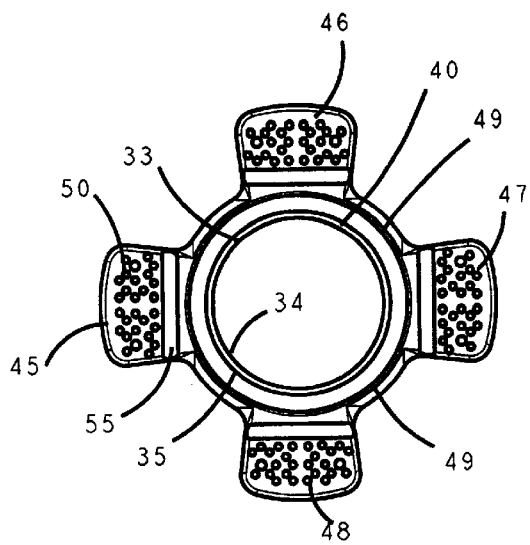
FIG. 4 is a top view of the constrictor ring.

As shown in FIG. 2, a tubular shaped loader 60 having an open end 62 with a diameter of about one and a half (1½) inches is provided to facilitate placement of the constrictor ring around the base 14 of the male genital 10. The constrictor ring 30 is inserted around a narrow end 64 of the loader 60. The individual can then grip the handles 45–48 and slide the constrictor ring 30 down the length of the loader toward the open end 62. The larger diameter of the open end 62 stretches the diameter of the tubular and conical portions 40 and 42 of the constrictor ring 30 to facilitate placement on the base 7 of the flaccid penis. The outer surface of the loader 60 may have longitudinal grooves 66 running down the length of the loader, or it may have a smooth finish. A radial alignment groove 68 having a depth of about an eighth (1/8) is formed in the outside surface near the open end 62 of the loader 60. The interaction between the alignment groove 68 and the stretched constrictor ring 30 is believed to cause the ring to quickly snap off the loader 60 when the ring is pulled past the alignment groove and over the edge of the open end 62 of the loader.

As shown in FIGS. 8–13, the diaphragm seal 80 is made of an integral piece of soft, durable and flexible rubber to facilitate comfort and bending and stretching during use. Although the diaphragm seal 80 is preferably made of synthetic natural rubber, it should be understood that other materials having similar qualities may be used. A product similar to the diaphragm seal 80 used in the present invention is available through Da Goang Assorted Co., Ltd. of Taipei, Taiwan.

The Diaphragm seal 80 has a tubular wall 82 that is molded to have a natural generally tubular shape. The tubular wall 82 has inside and outside surfaces 84 and 85 and inner and outer ends 87 and 88. The tubular wall 82 and inner and outer ends 87 and 88 are substantially centered about a central axis 90.

A shank 92 having a tear drop shaped cross-sectional area forms the inner end 87 of the diaphragm seal 80 and defines an inner opening 94 having a predetermined diameter. The tear drop shaped shank 92 has inside and outside surfaces 95 and 96. The tear drop shaped shank 92 has a length of about 8 millimeters and a thickness of about 2.5 millimeters. The length of the tear drop shaped shank 92. The tear drop shaped shank is substantially parallel to and centered about the central axis 90 of the diaphragm seal 80. The tear drop shaped shank 92 is disigned so that a portion of its length 98 running along either its inside of outside surface 95 or 96 engages the outside surface 35 of the tubular portion 40 of the constrictor ring 30.

A shank 100 having a substantially round cross-secional area forms the outer end 88 of the diaphragm seal 80 and defines an outer opening 102 havig a predetermined diameter. The diameter of the outer opening 102 is larger than the diameter of the inner opening 87. The round shaped shank 100 has a surface 104 and is substantially centered about axis 90. The tear drop shaped shank 92 has a diameter of about 4 millimeters. The surface 104 of the round shank 100 remains flush with the outside surface 85 of the diaphragm seal 80 and projects inwardly from the inside surface 84. The amount of material forming the round shank 199 is about the same as the amount of material forming the tear drop shaped shank 92.

The tubular wall 82 has a first or top conical portion 110 located near outer end 88, a second or middle conical portion 112, and a third or bottom portion 114 located near inner end 87. Top portion 119, middle portion 112, bottom portion 114 are integrally formed and have a substantially uniform thickness of about 1 millimeter. Two handles 119 are integrally formed to the diaphragm seal 80 and project outwardly from the round shank 100. The shanks 92 and 100 are thicker and more stretch resistant than the walls of the tubular 82.

FIGS. 8–10 show the diaphragm seal 80 in a relaxed position 120. This is the natural molded position of the diaphragm seal 80. The diaphragm seal tends to return to this position when compressed, twisted or otherwise altered. In the relaxed position 120, the top portion 110 of the tubular wall 82 has a given slope or degree of incline with respect to the central axis 90. The middle portion 112 has a greater slope with respect to the central axis 90. The bottom portion 114 has a third slight degree of slope with respect to the central axis 90. In the relaxed position 120, the inner end 87 is spaced a predetermined distance along the center axis 90 from the outer end 88.

FIG. 11–show the diaphragm seal 80 in a stable collapsed position 125. Although this is not its natural molded position, the diaphragm seal 80 is designed to remain stable in this collapsed position 125, until the inner end 87 or tear drop shaped shank 92 is pushed or pulled out or away from the outer end 88 or round shank 100. In the compressed position 125, the slope of the top portion 110 of the tubular wall 82 is reduced toward the outer end 88. The middle portion 112 has been bent back toward the outer end 88 so that it now has a negative slope or opposite degree of incline with respect to the central axis 90. The bottom portion 114 and tear drop shaped shank 92 generally retain their shape and degree of slope with respect to the central axis 90. In the collapsed position 125, the inner end 87 and tear drop shaped shank 92 are drawn a predetermined distance along the center axis 90 toward the outer end 88 and round shank 100.

Figure 17:
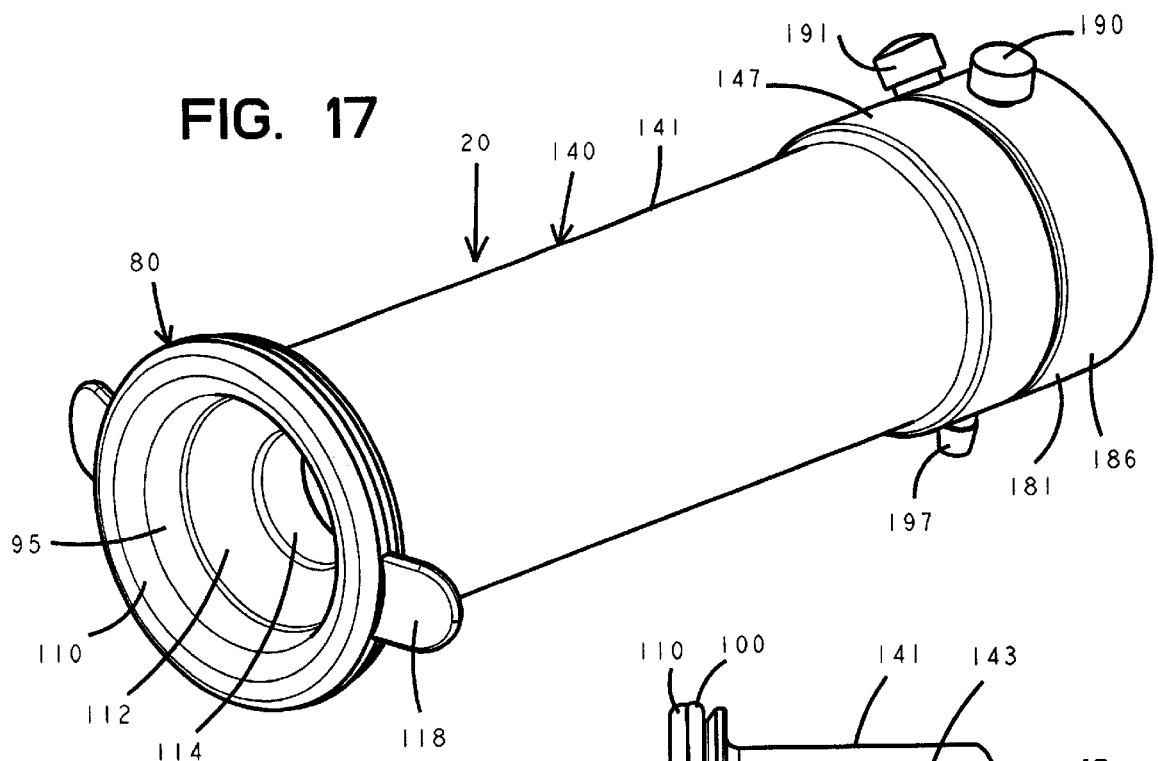
FIG. 17 is a perspective view showing the diaphragm seal placed over the open end of the double flange vacuum tube.
Figure 18:
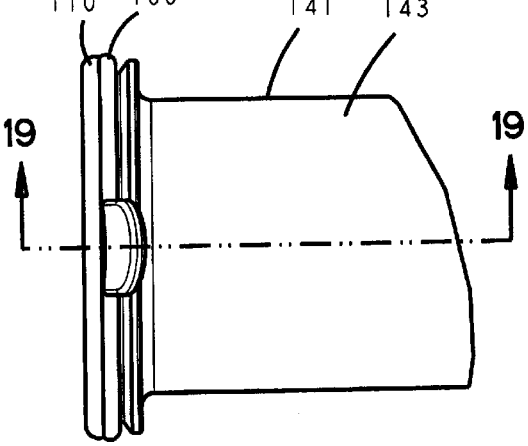
FIG. 18 is a partial side view showing the diaphragm seal placed over the open end of the double flange vacuum tube.
Figure 19:
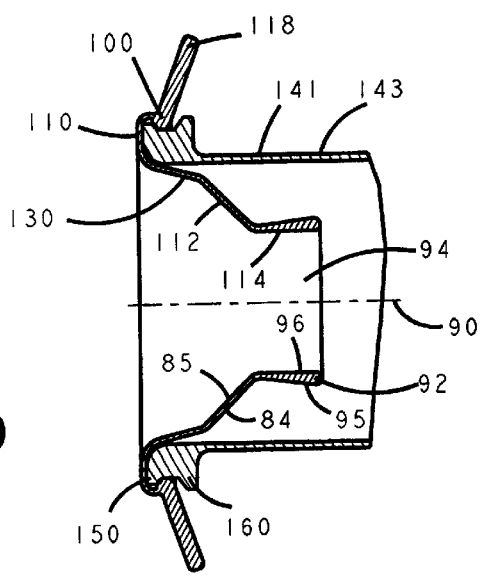
FIG. 19 is a cross-sectional view taken along line 19—19 of FIG. 18 showing the placement of the outer end of the diaphragm seal between the double flanges of the open end of the vacuum tube.
Figure 20:
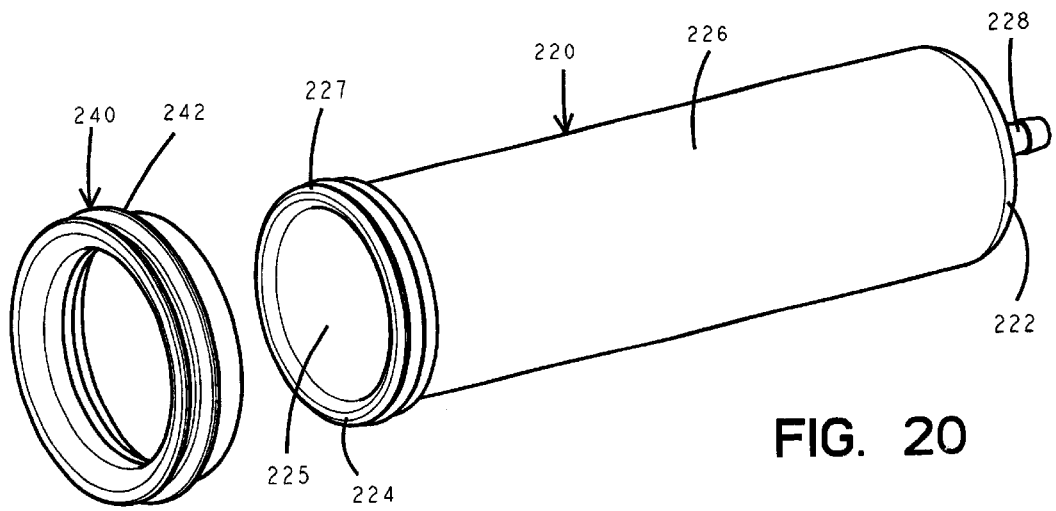
FIG. 20 is and exploded perspective view showing an adapter having a double flange design aligned to mate with the open end of conventional vacuum tube.
Figure 21:
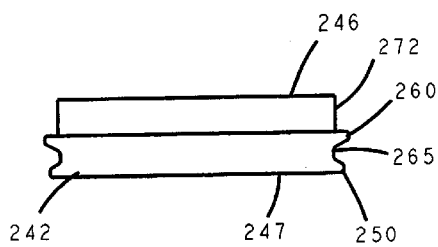
FIG. 21 is a side elevation view showing the adapter.
Figure 22:
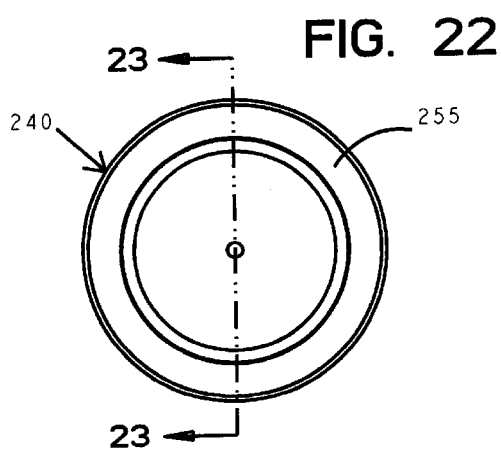
FIG. 22 is a front elevated view showing the adapter.
Figure 23:
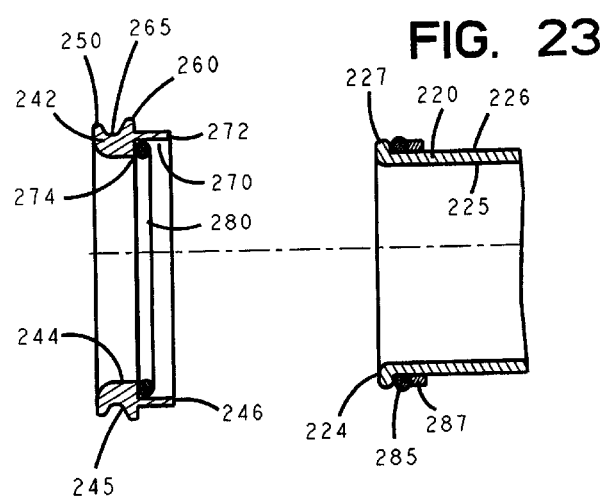
FIG. 23 is a cross-sectional view taken along line 23—23 of FIG. 22 showing the double flange adapter design aligned with a conventional vacuum tube.

FIGS. 17–19 show the diaphragm seal 80 secured to the vacuum tube 140 in an inverted position 130. The round shank 100 forming the outer opening 102 helps maintain the air tight seal between the outer end 88 of the diaphragm seal 80 and the vacuum tube 140, as discussed below. The thicker and more stretch resistant outer shank 100 helps maintain the air tight seal between the outer end 88 of the diaphragm seal 80 and the vacuum tube 140. The outside surface 96 of the tear drop shaped shank 92 is now facing toward the central axis 90 and forms the inner opening 94. The handles 118 enable the individual using the device to easily release the diaphragm seal 80 from the vacuum tube 220 after the male genital has been inflated to an erect position, as will be discussed later.

Figure 6:
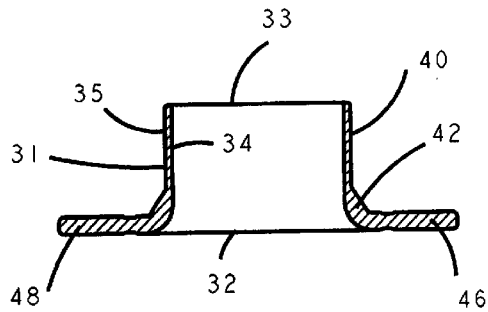
FIG. 6 is a cross-sectional view taken along line 6—6 of FIG. 5.
Figure 5:
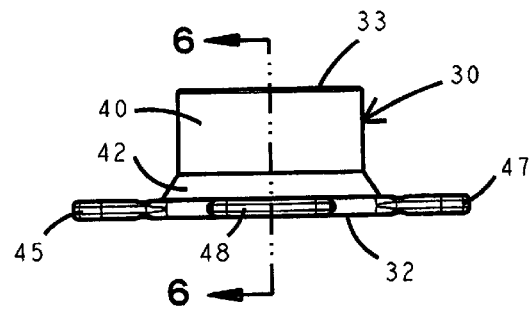
FIG. 5 is a side elevation view of the constrictor ring.
Figure 7:
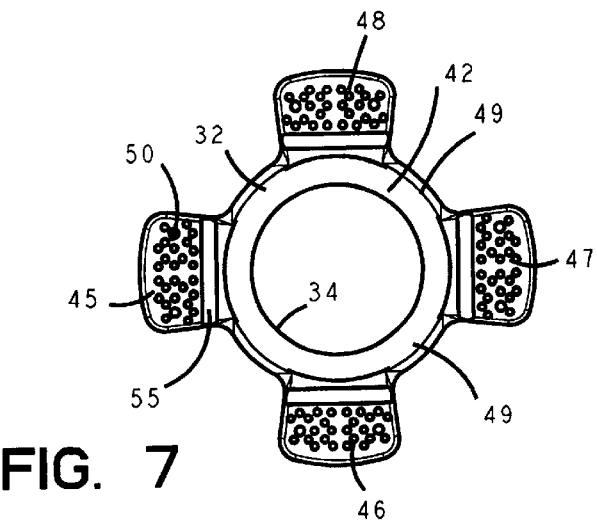
FIG. 7 is a bottom view of the constrictor ring.
Figure 14:
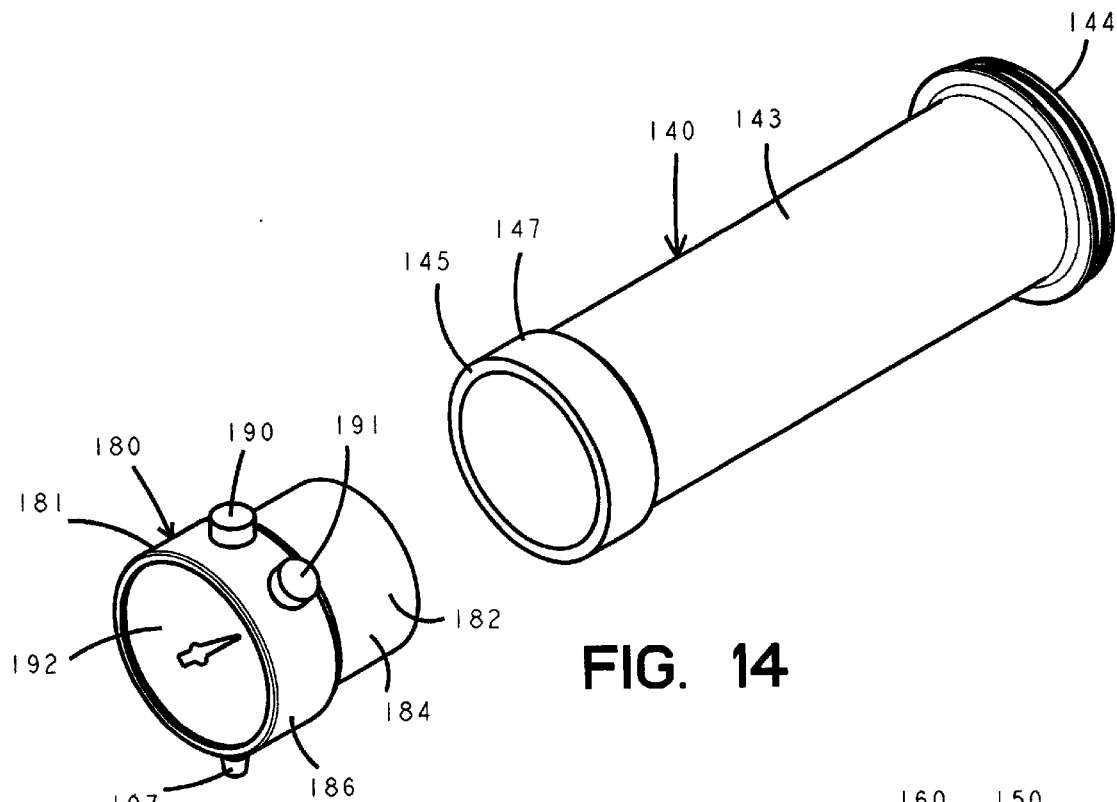
FIG. 14 is an exploded perspective view showing the double flanged vacuum tube aligned with the control plug.
Figure 15:
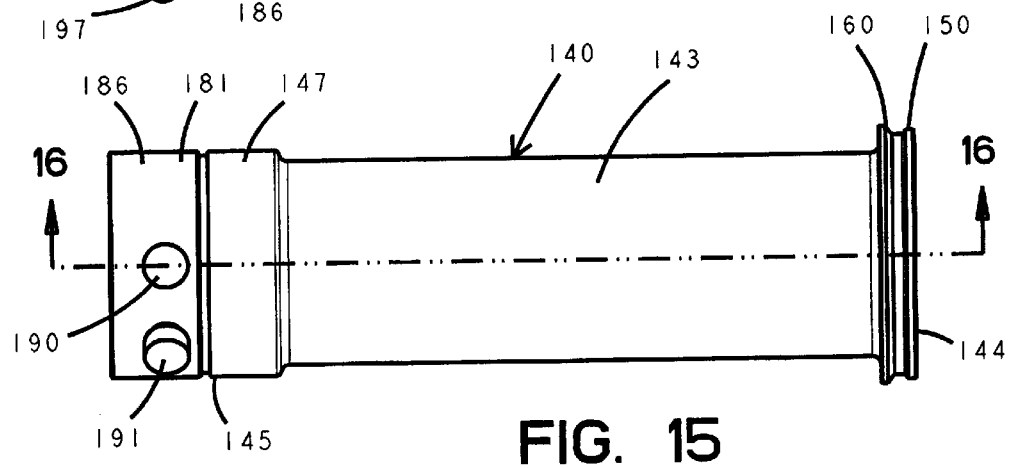
FIG. 15 is a side elevation view showing the double flanged vacuum tube secured to its open end and a control plug sealing the outer end.
Figure 16:
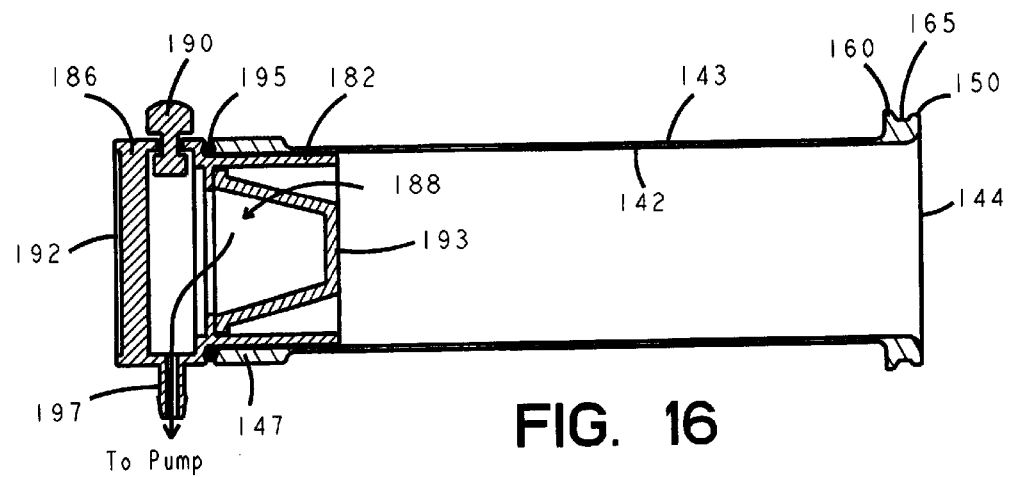
FIG. 16 is a cross-sectional view taken along line 16—16 of FIG. 15 showing the rounded inside surface of the one end of the double flange vacuum tube, the filter, the vacuum relief valve and the air flow passageway in the control plug.

The vacuum tube 140 and control plug 180 are shown in FIGS 14–1 6. The vacuum tube 140 has a generally cylindrically shaped tubular body 141. The tubular shaped body 141 has an inside surface 142 for receiving the male genital 10, and outside surface 143 and open ends 144 and 145 having inside diameters of about two inches. The tube 140 is preferably made of a rigid, transparent polypropylene having a thickness of about 0.1 inch. The tube 140 is designed to maintain its shape when at least about 24 inches of mercury in vacuum pressure are achieved inside the tube. The tube 140 has a thicker, more robust portion 147 near opening for receiving the control plug 180. The tube 140 is sized and shaped to accommodate the male genital 10 of a variety of individuals.

First and second flanges 150 and 160 extend radially in a direction substantially perpendicular to the outside surface 143 of the vacuum tube 140. The first flange 150 has an outer surface 152 that is flush with open end 144 of the tube 140. The inside surface 142 of the open end 144 is curved to form a rounded portion. The rounded portion has a radius of about 1/4 inch, but could be larger if desired. The outer surface 152 of the flange 150 and the rounded portion form a blunt area 155 that can be pressed against the groin of an individual with relatively minimal pain when high vacuum pressures are achieved.

The second flange 160 is spaced a predetermined distance from the first flange 150 to form a substantially U-shaped, positioning channel 165 for receiving the round shank 100 of the diaphragm seal 80. The first flange 150 has a height of about ⅜from the inside surface 142 of the tube 140. This height permits the round shank 100 to be stretched over the fist flange 150 and snap fit into the positioning channel 165. The second flange 150 has a greater height than the first flange 150 and snap fit into the positioning channel 165. The second flange 160 has a greater height than the first flange 150. This greater height does not readily permit the round shank 100 to stretch over the second flange 160. This facilitates the placement and seating of the rounded shank 100 in the positioning channel 165 so that it rests against the first flange 150. The inside surface 84 of the first portion 110 of the diaphragm wall 82 wraps around and lays against the outer surface 152 of the first flange 150 and the rounded portion of the open end 144 of the tube 140. The first flange 150 has a uniform height and thickness around the circumference of the open end 144 of the tube 149. The blunt area 155 is also uniformly shaped around the circumference of the open end 144. This causes the diaphragm seal 80 to secure to over the open end 144 of the tube 140 so that the center axis 90 of the diaphragm seal 80 aligns with a center axis 170 of the vacuum tube 140 as shown in FIG. 19. This snap fit securement also produces a substantially air tight seal between the diaphragm seal 180 and the tube 140.

Control plug 180 has a main body 181 containing a first portion 182 with an outer surface 184, and a second portions 186. The outer surface 184 of the first portion 182 has a diameter sized to be snugly received into the open end 145 of the vacuum tube 140. The second portion 186 extends from the open end 145 of the tube 140. Air can flow through the control plug 180 via a passage way 188. A vacuum pressure relief valve 190 is located on the second portion and is in communication with the passage way 190. An electric switch 191 is also located on the second portion for activating and deactivating the pump 200 that removes air from the inside of the tube 140. A pressure gauge 192 is located on the face of the control plug 180 but could be located elsewhere if desired. The control plug 180 includes an air filter 193 for removing particles such as powder that might otherwise clog the passageway 188, hose 202 or pump 200. The second portion 186 has a slightly larger diameter to create a ridge against which a gasket 104 can be placed. Gasket 195 is compressed between this ridge and the open end 145 of the tube 140 to form a substantially air tight seal between the tube and the control plug 180. The control plug 180 includes a nippled outlet 197 at the end of the passage way 190.

The pump 200 is used to evacuate or remove air from the vacuum tube 140. A flexible hose 292 connects the nippled opening 197 of the control plug 180 to the pump 200. The pump 200 should be capable of achieving vacuum pressure in excess of 24 inches of mercury. The pump 200 should also have a safety valve or vacuum limiter (not shown) set to open at 24 inches of mercury to prevent harmful vacuum pressures from being imparted to the individual during use. In this way, the pump 200 can experience a reduction in achievable vacuum pressure due to wear and tear over time, without affecting the performance of the device 20. While the preferred embodiment is shown to use an electric pump 200 for removing or evacuating air from the tube 140, it should be understood that other evacuating means, such as a hand pump, could be employed without departing from the invention.

FIGS. 20–23 show an adapter ring 240 for use with a conventional vacuum tube 220. The conventional vacuum tube 220 is a generally cylindrically shaped tube having a predominantly closed end 222, an open end 224 with a diameter of about two inches and an inside surface 225 for receiving the male genital 10. The tube 229 is preferably made of a rigid, transparent plastic having a thickness of about 0.1 inch. The tube 220 is designed to maintain its shape when at least about 24 inches of mercury in vacuum pressure is achieved inside the tube. An outwardly projecting lip 227 is formed around a perimeter of the open end 224. The lip 227 has a height of about 0.25 of an inch and its edges are rounded for comfort. The predominantly closed end 222 of tube 220 has a nippled opening 228 through which air is removed from inside the tube 220. The tube 220 is sized and shaped to accommodate the male genital of a variety of individuals.

The adapter ring 240 includes a ring 242 with an inside surface 224 for receiving the male genital 20, and outside surface 245, and inner and outer ends 246 and 247 having inside diameters of about two inches. The adapter ring 240 is preferably made of a rigid, transparent polypropylene. The adapter ring 240 is designed to maintain its shape when at least about 24 inches of mercury in vacuum pressure is exerted on the ring. The structure of the adapter ring 240 is similar to that of the flared open end 144 of the vacuum tube 140 and includes first and second flanges 250 and 260.

First and second flanges 250 and 260 are located at the outer end 247 of the adapter ring 240. Both flanges 250 and 260 extend radially from in a direction substantially perpendicular to the longitudinal axis and outside surface 245 of the adapter ring 240. The first flange 250 has an outer surface 252 that is flush with outer end 247 of the adapter ring 240. The inside surface 244 of the outer end 247 is curved to form a rounded portion. The rounded portion has a radius of about ¼ inch, but could be larger if desired. The outer surface 252 of the flange 250 and the rounded portion form a blunt area 255 that can be pressed against the groin of an individual with relatively minimal pain.

The second flange 260 is spaced a predetermined distance from the first flange 250 to form a substantially U-shaped, positioning channel 265 for receiving the round shank 100 of the diaphragm seal 80. The first flange 259 has a height of about ⅜from the inside surface 244 of the adapter ring 240. This height permits the round shank 100 to be stretched over the shank and snap fit into the positioning channel. The second flange 260 has a greater height than the first flange 250. This greater height does not readily permit the round shank 100 to stretch over the second flange 260. This facilitates the placemat and seating of the rounded shank 100 in the positioning channel 265 so that is rests against the first flange 250. The inside surface 84 of the first portion 110 of the diaphragm wall 82 wraps around and lays against the outer surface 252 of the first flange 250 and the rounded portion of the outer end 247 of the ring 240. The first flange 250 has a uniform height and thickness around the circumference of the outer end 247 of the adapter ring 240. The blunt area 225 is also uniformly shaped around the circumference of the outer end 247. This causes the diaphragm seal 80 to secure to over the outer end 247 of the adapter ring 240 so that the center axis 90 of the diaphragm seal 80 aligns with a center axis 269 of the ring and conventional vacuum tube 220. This snap fit securement also produces a substantially air tight seal between the diaphragm seal 80 and the adapter ring 240.

The inner end 246 of the adapter ring 240 includes a recess 270 that forms a longitudinal flange 272 extending around the circumference of the inner end of the ring. The longitudinal flange 272 has an inside surface 244 that defines an outer opening having a diameter sized to snugly receive the outwardly projecting lip 227 of the open end 224 of the conventional vacuum tube 220. The recess 270 has an inner end 274 against which a first gasket 280 may be placed. When vacuum pressure is applied, the gasket 280 is compressed between the adapter ring 240 and the open end 224 of the conventional vacuum tube 220 to form a substantially air tight seal. A second or alternate gasket 285 may be secured around the outside surface 226 and against the lip 227 of the conventional vacuum tube 220. The gasket is sized to snugly engage the inside surface 244 of the longitudinal flange 272 of the adapter ring 240 to produce a substantially air tight seal between the adapter ring 240 and the conventional vacuum tube 220. A locking member 287 may be provided to help secure the alternate gasket 285 to the vacuum tube 229.

OPERATION OF THE DEVICE

Although the operation of the present invention should be understood based on the above description, the following is provided to more easily explain the operation of the device 20. The device 20 can be provided in the form of a kit that can be purchased and taken to the privacy of an individual's home. The kit includes the vacuum tube 140, control plug 180 and pump 200, a plurality of diaphragm seals 80 each having an inner opening 94 of varying diameter, and a plurality of constrictor rings 30 each having an outer end 33 of varying diameter that cooperates with one of the diaphragms. The individual can then select the cooperating diaphragm seal 80 and constrictor ring 30 that comfortably and effectively fit their male genital. The kit may also contain an adapter ring 240 in lieu of the tube 140, control plug 180 and pump 200.

As shown in FIG. 2, the appropriate constrictor ring 30 is inserted onto the loader 60 and slid down to its open end 62 by gripping and pulling on the handles 45–48. A dry powder, such as baby powder may be used to help decrease the force needed to slide the constrictor ring down the loader 60. The constrictor ring 30 is positioned over the radial alignment groove 68 near the open 62 end of the loader 60. Any kinds of distortion in the tubular and conical portions 40 and 42 of the constrictor ring caused by pulling on the handles 45–48 are removed when the ring is positioned over the alignment ring. The flaccid penis 10 is then inserted into the open end 62 of the loader 60, and the constrictor ring 30 is slid off the loader and onto the genital 10 as close to its base 14 as possible by using the handles 45–48, the individual can work the constrictor ring 30 into an optimal position where the inside surface 34 of the handles rest against, but do not press into, the surface of their groin 18. The constrictor ring should now be applying a predetermined amount of pressure to the surface 13 of the male genital.

Figure 25:
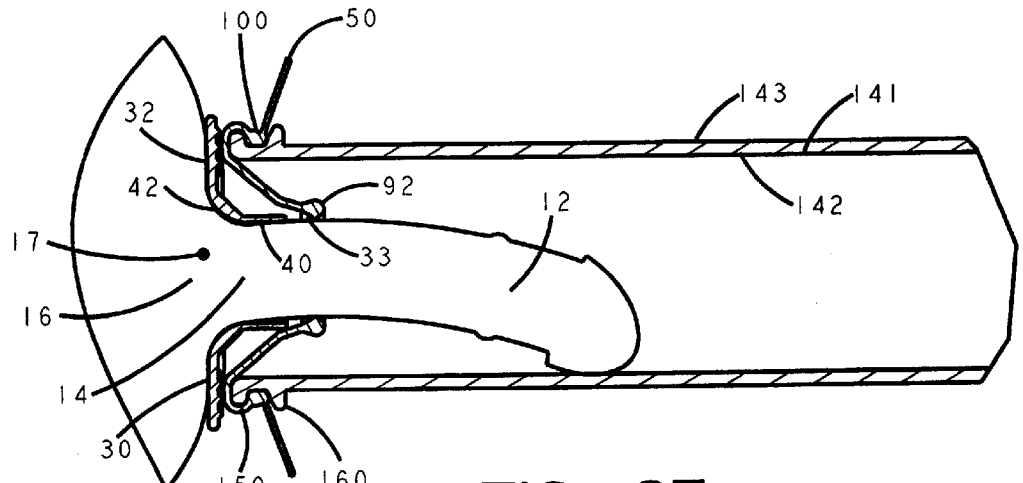
FIG. 25 is a cross-sectional view showing the penile erection device installed around the flaccid male genital with the diaphragm sealing directly around the male genital.

As shown in FIG. 24, the tip of the male genital 10 is than aligned with and placed against the opening in the inner end 87 of the diaphragm seal 80. The diaphragm seal is already secured to the open end 144 of the vacuum tube 140 as shown in FIG. 25. Initially, the outside surface 96 of the rear drop shaped shank 92 of the inverted diaphragm 80 engages and seals against the surface 13 of the male genital 10. The seal is made along the engagement area 98 of the tear drop shaped shank 92. This seal enables the pump to obtain an intermediate amount of vacuum pressure inside the vacuum tube 140. Depending on the diameter size of the inner opening 94 of the diaphragm seal 80 selected and the characteristics of the male genital 10 of the particular individual, the engagement area 98 should now be applying a predetermined amount of pressure to the surface 13 of the male genital. This intermediate amount of vacuum pressure causes the genital 10 to begin inflating and begins to draw the root 16 of the genital 10 toward the constrictor ring 30. The vacuum pressure also causes the constrictor ring 30 to move toward the inner end 87 of the diaphragm 80.

Figure 26:
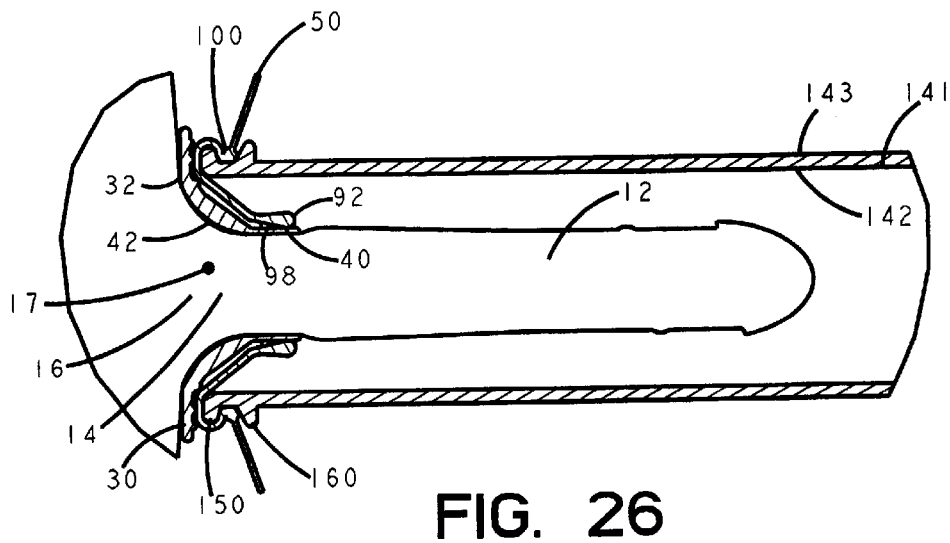
FIG. 26 is a cross-sectional view showing the penile erection device installed around a partially inflated male genital after a first predetermined amount of vacuum pressure has been produced inside the vacuum tube, with the root of male genital and the constrictor ring beginning to be drawn into the tube, and with the diaphragm sealing against the constrictor ring beginning to be drawn into the tube, and width the diaphragm sealing against the constrictor ring to form a substantially air tight seal.
Figure 27:
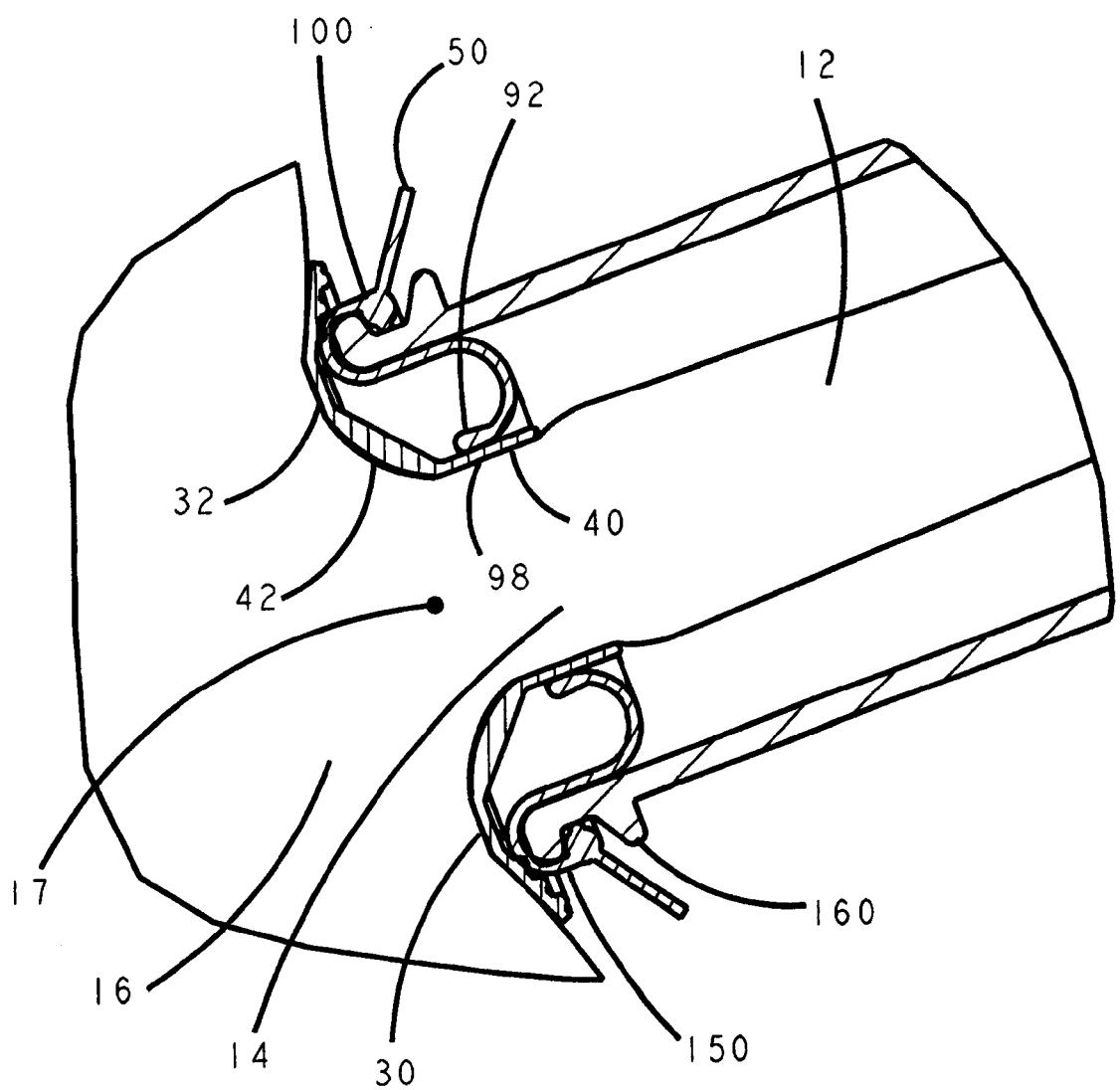
FIG. 27 is an enlarged cross-sectional view showing the diaphragm after a second predetermined amount of vacuum pressure as been produced inside the vacuum tube, with the inner end of the diaphragm has inverted so that the diaphragm forms an "S" shape, and with a portion of the root of the male genital drawn into the constrictor ring.

When a first predetermined amount of vacuum pressure is achieved inside the vacuum tube 140, the engagement area 98 of the tear drop shaped 92 of the diaphragm 80 engages the outer end 33 of the constrictor ring 30 and slides up onto and seals against the outer surface 35 of the tubular portion 40 of the constrictor ring as shown in FIG. 26. The tubular portion 40 of the constrictor ring 30 and the engagement portion 98 of the rear drop shaped shank 92 now combine to produce a larger amount of pressure to the surface 13 of the male genital 10 directly beneath the tubular portion 40 and engagement area 98. This forms a substantially air tight seal and enables the pump 200 to produce a greater amount of vacuum pressure inside the vacuum tube 140. The greater amount of vacuum pressure can be in the range of about 17 to 24 inches of mercury below atmospheric pressure. The greater vacuum pressure causes the genital 10 to achieve a more inflated state and draws the root 16 of the genital 10 into the constrictor ring 30 as exemplified by root point 17. The greater vacuum pressure is also believed to cause some of the root 10 cause the shaft 12 to raise up to produce a more natural and usable erection as shown in FIG. 27. As the male genital 10 continues to inflate, it tends to grow in diameter. Increases in diameter are resisted by the tubular portion 40 of the constrictor ring 30 and the tear drop shaped shank 92 which now combine to apply total amount pressure to the surface 13 of the male genital 10. Although the percentage of contribution of total pressure applied by the tubular portion 40 or tear drop shaped shank 92 will vary depending on the size of the diameter of the ring and shank selected by the individual, a roughly even 50/50 contribution is thought to be preferable.

After the diaphragm 80 seals against the constrictor ring 30 and a second predetermined amount of vacuum pressure of about 17 inches of mercury is achieved inside the vacuum tube 140, the diaphragm 80 may invert so that the diaphragm forms an "S" shape as shown in FIG. 27. After the inversion into the collapsed "S" shape as occurred, the inside surface 84 of the tear drop shaped shank 92 is in contact with and seals against the outside surface 35 of the constrictor ring 30. The amount of vacuum pressure needed to achieve the first and second predetermined amounts of pressure will vary from individual to individual depending on a variety of factors such as the size, shape and characteristics of the male genital 10, diaphragm 80 and constrictor ring 30.

The pump 200 is then turned off and the vacuum pressure relief valve 190 is depressed to release the vacuum pressure from inside the tube 140. The individual then disconnects the diaphragm seal 80 from the vacuum tube 140 by use of the handles 118, as shown in FIG. 8. The diaphragm seal 80 collapses into its collapsed position 125 against and remains on the constrictor ring 30. The male genital 10 remains in its natural erect position after the vacuum tube 140 is removed because it is believed that some of the root 16 and 17 has been drawn into the constrictor ring 30 so that the blood is retained in the inflated root. The constrictor ring 30 and diaphragm seal continues to apply the total amount of pressure to the surface 13 of the male genital 10 beneath the tubular portion 40 of the ring 30 and the engagement area 98 of the tear drop shaped shank 92.

Figure 28:
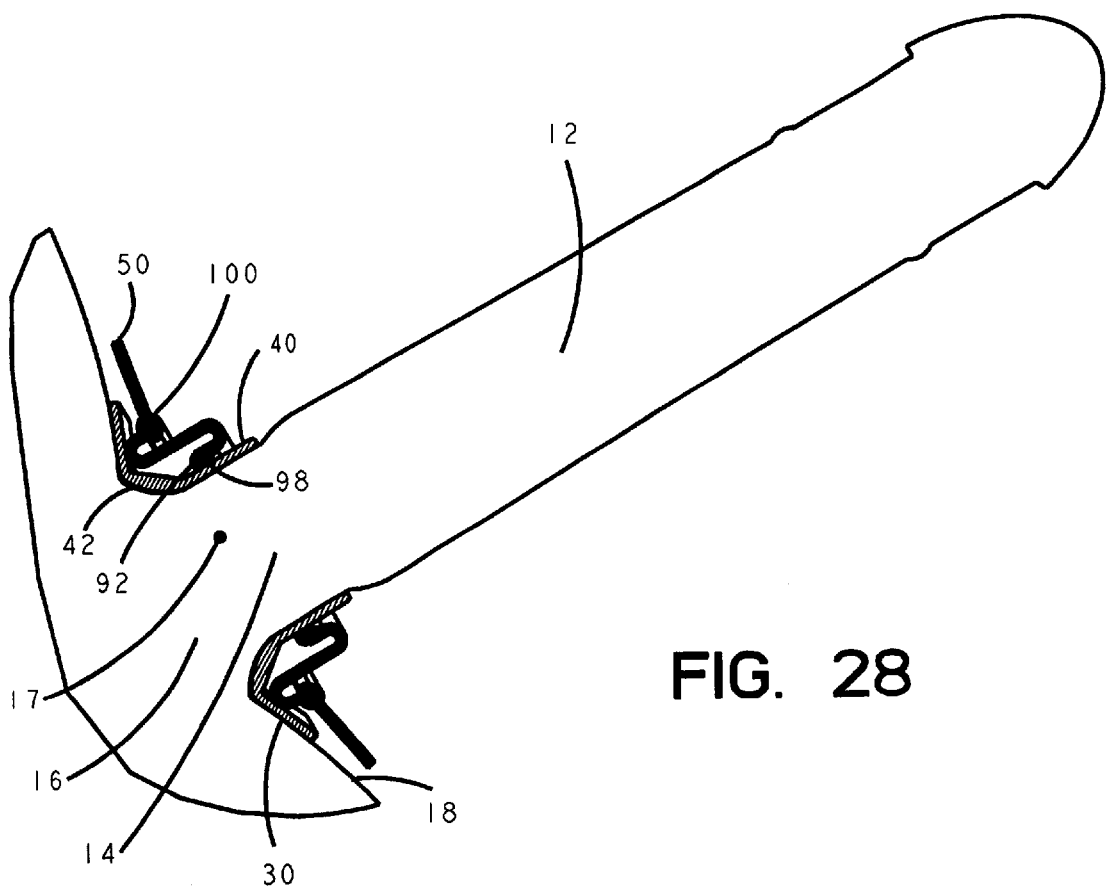
FIG. 28 is an enlarged cross-sectional view showing the constrictor ring secured to the base of the penis, the diaphragm seal being in a collapsed position, and the diaphragm released from the vacuum tube.
Figure 29:
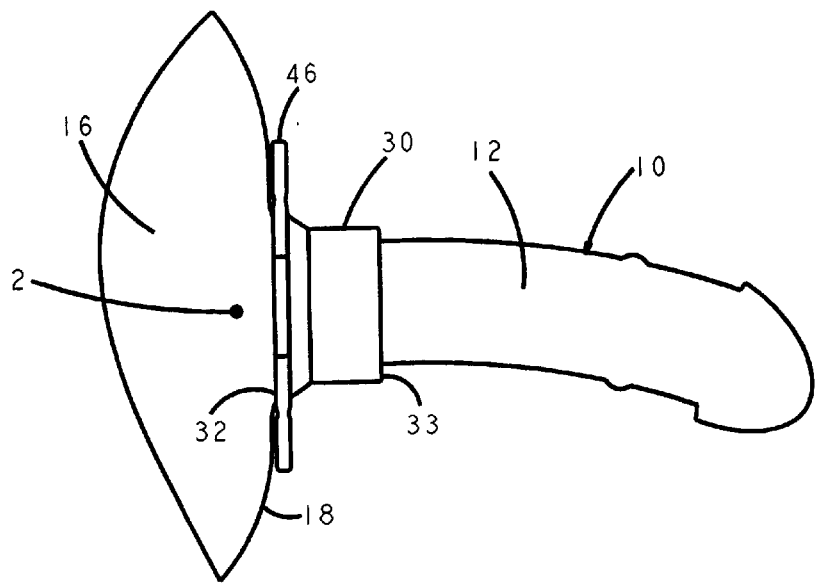
FIG. 29 is a side view showing a constrictor ring secured to the base of a partially deflated male genital after the diaphragm seal has been removed.

Removal of the diaphragm seal 80 and constrictor ring 30 is easily accomplished. Even though the male genital 10 remains inflated as in FIG. 28, the diaphragm seal 80 may be pulled off relatively easily by pulling on the handles to return the diaphragm seal to its relaxed position 120. Once in this relaxed position 120, the diaphragm seal 80 can be pulled off the male genital 10 relatively easily as it has a sloped tubular wall 82 and is only exerting roughly half the total pressure to the surface of the male genital. Once the diaphragm seal 80 has been removed, a reduction in pressure around the base 14 of the genital 10 permits the genital to deflate to a reduced less swollen state as in FIG. 29. When the genital 10 is in this reduced state, the constrictor ring can be removed relatively easily.

Repeated use of the penile erection device 20 is believed to cause the male genital 10 of an individual having a given erect size to increase to an enlarged erect size. Thus is believed to be accomplished by repeatedly exposing the male genital 10 to vacuum pressure of about 16 inches of mercury or more for a predetermined time interval.

It will be understood that the invention may be embodied in other specific forms without departing from the spirit or central characteristics of the invention. The present examples and embodiments of the invention are to be considered in all respects as illustrative and not restrictive, and the invention is not to be limited to the details given herein.

Having described our invention, what we claim as new and desire to secure by Letters Patent of the United States is:

1. An adapter for use with a conventional vacuum tube for a non-invasive penile erection device, the conventional vacuum rube having an open end with a predetermined diameter and an inside adapted to receive a male genital, said adapter comprising:

a ring having inside and outside surface and inner and outer ends, said ring being adapted to matingly engage the open end of the vacuum tube and received the male genital;

a first flange located proximal to said outer end of said ring and protecting radially from said outside surface of said ring; and, a second flange spaced a predetermined distance form said first flange and protecting radially from said outside surface of said ring, said first and second flanges forming a channel.

2. The adapter of claim 1, and wherein the open end of the conventional vacuum tube has a perimeter, and wherein said inner end of said ring has a recess that forms a longitudinal flange with a predetermined diameter, said longitudinal flange matingly receiving the perimeter of the open end of the conventional vacuum tube.

3. The adapter of claim 2, and wherein the conventional vacuum tube has inside and outside surfaces, and wherein said recess is formed along said inside surface proximal said inner end of said ring, and the outside surface of the vacuum tube engages said inside surface of said ring.

4. The adapter of claim 3, and wherein the conventional vacuum tube has a lip proximal the open end and extending radially form the outside surface of the vacuum tube, and further comprising a gasket secured over the outside surface of the vacuum tube proximal the lip, said gasket being adapted to matingly engage said inside surface of said recess of said ring to form a substantially air tight seal between said ring and the vacuum tube.

5. The adapter of claim 4, and further comprising an abutment secured over the outer surface of the vacuum tube and spaced apart a predetermined distance from the lip of the vacuum, said abutment and the lip forming a channel for holding said gasket.

6. The adapter of claim 5, and wherein said inside surface of said outer end of said adapter is rounded, and said first flange has an outer surface that forms a radially extending blunt area, said rounded outer end and said blunt area being adapted to comfortably engage a groin of an individual.

7. The adapter of claim 6, and wherein said rounded outer end has a radius of at least about ¼ inch, and said outer surface of said first flange has a radial height of at least about ⅜ from said inside surface of said ring.

* * * * *